US006221223B1

(12) United States Patent
Tzeng et al.

(10) Patent No.: US 6,221,223 B1
(45) Date of Patent: Apr. 24, 2001

(54) METHOD OF QUANTITATIVE ANALYSIS FOR THURINGIENSIN BY CAPILLARY ELECTROPHORESIS

(76) Inventors: Yew-Min Tzeng; Cheng-Ming Liu, both of No. 1, Section 2, University Ave., Shoufeng, Hualien (TW)

( * ) Notice: Subject to any disclaimer, the term of this patent is extended or adjusted under 35 U.S.C. 154(b) by 0 days.

(21) Appl. No.: 09/183,900

(22) Filed: Oct. 30, 1998

(30) Foreign Application Priority Data

Jun. 11, 1998 (TW) .............................................. 87109276

(51) Int. Cl.[7] ............................................... G01N 27/26

(52) U.S. Cl. ........................................ 204/451; 204/456

(58) Field of Search .................................. 204/451, 456, 204/461, 452

*Primary Examiner*—Jill Warden
*Assistant Examiner*—Alex Noguerola

(74) *Attorney, Agent, or Firm*—Pacific Law Group LLP; Chi Ping Chang

(57) ABSTRACT

Quantitative analysis for thuringiensin by capillary electrophoresis ("CE') was demonstrated. CE is a suitable separation technique for thuringiensin because of its high resolution, great efficiency, rapid analysis and small consumption of sample. Tryptophan, an aromatic amino acid sharing a similar UV absorptive spectrum as thuringiensin, was used as an internal standard to avoid some inaccurate results caused by the questionable stability of purified thuringiensin. A mixed amount of tryptophan was mixed with varied amount of newly made thuringiensin standards for CE analysis. The electropherograms showed that the peak of tryptophan appeared around 8 minutes, which is 6 minutes earlier than the peak of thuringiensin. The peak area ratio between thuringiensin and tryptophan is proportional to the amount of thuringiensin in the mixture. The linear regression has been established to assess the peak area ratio that can be used to quantify the concentration of thuringiensin. This method provides a faster and more accurate quantitative analysis than the traditional methods.

3 Claims, 6 Drawing Sheets

METHOD OF QUANTITATIVE ANALYSIS FOR THURINGIENSIN BY CAPILLARY ELECTROPHORESIS

BACKGROUND OF THE INVENTION

1. Field of the Invention

The present invention demonstrates the method of quantitative analysis for thuringiensin by capillary electrophoresis (CE) and use Tryptophan as an internal standard.

2. Description of the Prior Art

Thuringiensin is the β-exotoxin secreted by *Bacillus thuringiensis*, and is one kind of nucleotide analogue, it's poison against insects and Nematoda, mite and pertains to a broad spectrum of biological insecticide. There is a large potential market. So far there are some breakthrough in fermentation and recovery technology. However, so far there are no accurate, rapid and effective method of quantitative analysis. HPLC has replaced the prior bioassay as quantitative assay is time-consuming and labor intensive.

HPLC (high performance liquid chromatography) has been used to detect *Bacillus thuringiensis* ever since 1982. In the beginning the technology is not mature such that it lacks specificity to complicated mixing of fermentation solution and the sensitivity is low. Then buffer gradient elution technique was used for improvement, but it's still time-consuming. Recently people found that the concentration of thuringiensin is proportional to the peak area in the eluting buffer which contains 50 mM Di-hydrogen potassium phosphate at 2.8 PH. And it takes only 20 minutes to complete the assay. The HPLC analysis of various concentrations of standards has shown that the concentration of thuringiensin is linearly proportional to the peak area. And the resultant chromatogram is quite repeatable and has good specificity. Therefore, it's an inevitable tendency that HPLC will replace the conventional bioassay.

There are still some disadvantages although HPLC is efficient. For example, it has to stabilize the baseline before the assay is started, and also the column is expensive with a limited lifetime. Recently, there is a new CE technique which can separate different molecules more rapidly, more accurately and can do qualitative & quantitative analysis. New CE techniques can speed up the analyzing time, simplify the analyzing process, and can make the analysis more efficient and accurate. For quantitative analysis of thuringiensin, a purified standards is required as reference. It's quite difficult to purify Thuringiensin due to the low molecular weight (MW=701) and low concentration in fermentation broth. In addition, the purified thuringiensin is unstable and thus becomes difficult to preserve. The present invention-Tryptophan or some Amino Acids such as tyrosine or phenylalanine are used as an internal standard, to replace the purified Thuringiensin for quantitative analysis.

SUMMARY OF THE INVENTION

The present invention demonstrates the method of quantitative analysis for thuringiensin by capillary electrophoresis (CE) and use Tryptophan as an internal standard.

BRIEF DESCRIPTION Of THE DRAWINGS

FIG. 1*a*) 25 mg/ml of thuringiensin secondary standards.

FIG. 1*b*) 12.5 mg/ml thuringiensin secondary standards.

FIG. 1*c*) 6.25 mg/ml of thuringiensin secondary standards.

FIG. 1*d*) 3.125 mg/ml of thuringiensin secondary standards.

1. The peak of Tryptophan appeared around 10.5 min.

2. The peak of thuringiensin appeared around 17.5 min.

Figure 3:
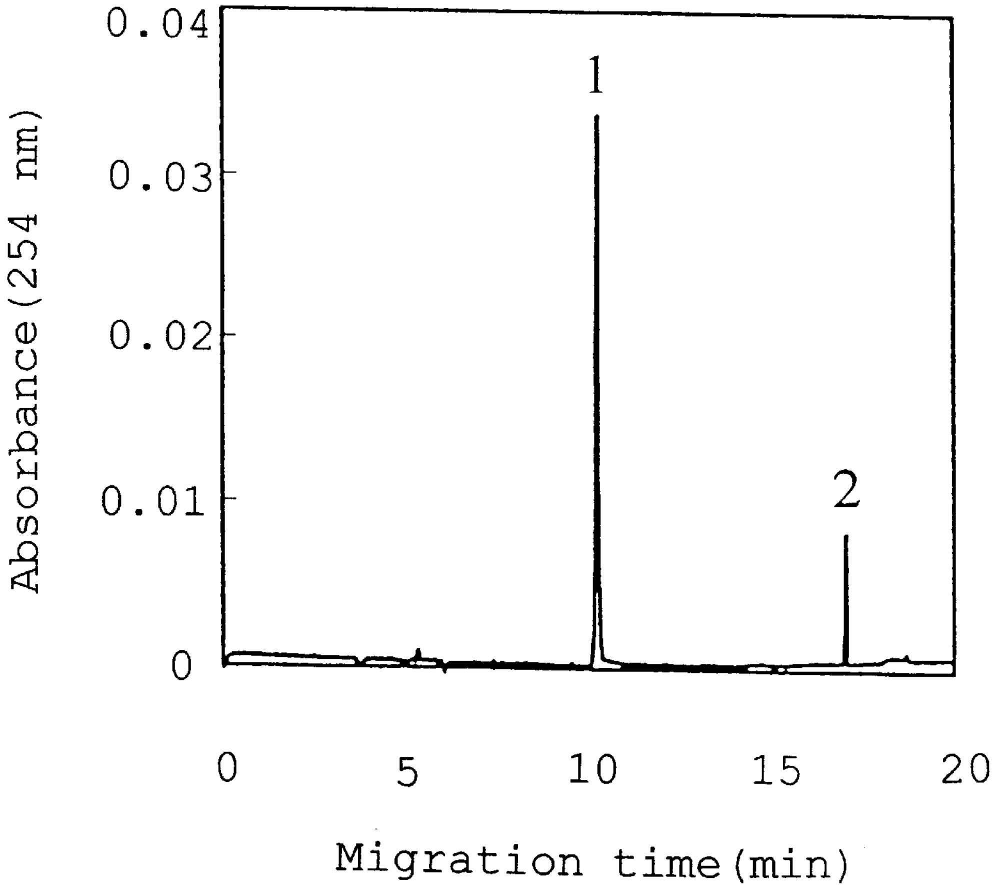

FIG. 3: The electropherograms of purified thuringiensin solutions mixed with the same volume of Tryptophan solution (5 M).

1. The peak of Tryptophan appeared around 10.5 min.

3. The peak of thuringiensin appeared around 17.5 min.

DETAILED DESCRIPTION OF THE PREFERRED EMBODIMENTS

Traditional quantitative analysis of thuringiensin such as bioassay was used as the standard, which needs more labor & equipment in raising the insects, and it takes 4–7 days to complete the assay. There are many factors that may affect the results of assay. Such as: 1) the species & age of insects, 2) the route of administration 3) the kind of feeding leaves and the way of handling 4) the incubating temperature and humidity during inoculation, 5) the number of insects and repeats, 6) the collection of results (recording date and justification of death), 7) the operation of personnel and the quality of insects, etc. Furthermore, the insects also differ by the variety of genetical species or geographic species. And some of then may be drug-resistant. Therefore the result of bioassay ($LC_{50}$) may have wide variance statistically.

The present invention applies a new technique-capillary electrophoresis (CE) for the quantitative analysis of thuringiensin. Since the analytes may have some extent of hydrophobicity in the solution, so micellar electrokinetic capillary chromatography (MECC) mode of CE has been used. Tryptophan, as an aromatic Amino Acids, has been applied as an internal standard.

Both thuringiensin and tryptophan absorb ultraviolet light at 254 nm. The migration time of tryptophan is faster than that of thuringiensin, therefore the former passes the detection window earlier than the later and both form two distinct peaks on the final electropherogram. Based on the above observations, tryptophan is suitable to be an internal standard. Under the present experimental conditions of the invention, the peak of tryptophan appeared around 8 min and the peak of thuringiensin appeared around 14 min. The peak area is proportional to the concentration of thuringiensin or tryptophan.

Mix certain preset amounts of thuringiensin standards with fixed amounts of tryptophan solution, inject the mixed solution into CE, after analyzing with micellar electrokinetic capillary chromatography mode of CE (detailed process please see "Application Example"), the peak of thuringiensin and tryptophan will appear on the resultant electropherogram. The peak area integration and peak area ratio can be calculated by computer software (System Gold, Beckman Instruments, Inc.). The correlation coefficient between the ratio and the concentration of thuringiensin along with the linear regression formula can be calculated from Excel (Microsoft Inc.). After setting up this formula, the quantitative analysis can be performed by mixing a fixed amount of tryptophan with a thuringiensin sample, and apply the same method and process under the same condition, the peak area ratio of thuringiensin to tryptophan can be obtained from the resultant electropherogram. And then the concentration of thuringiensin can be calculated from the standard linear regression formula. It is difficult to purify thuringiensin since its concentration is low in the fermentation solution and its molecules are small, in addition, the stability of purified thuringiensin is quite questionable. The peak on the electropherogram will probably change if the thuringiensin standards have been stored for a long time which may cause the problem such as getting wet, decomposition, and deterioration. Using "Internal Standard" to substitute purified thuringiensin may provide a convenient way for the quantitative analysis of thuringiensin. Tryptophan is an amino acid with high purity, high stability and easy to procure commercially which may be a good candidate as "Internal standard". Some additional advantages for using internal standard such as: 1) the amount of injection is easily corrected since the volume of injection varies each time. 2) the time that the peak of thuringiensin appearance may vary when the pH or the concentration of buffered electrophoresis solution prepared may not be the same. 3) ambient temperature or voltage from power supply may fluctuate which also may cause change of integration time. The peak area may vary if the migration time is changed. Therefore, the instability may be caused by the standards itself or by the analyzing condition and environmental factors. So, the internal standard may correct these deviations on a quantitative analysis. To choose internal standards, first we need to make sure that it has the same range of absorption wavelength as that of thuringiensin. Second, we need to make sure that no other physical or chemical reaction will take place. Third, the migration time should not be the same. The migration time of an ideal internal standards should be shorter than that of thuringiensin, so that the duration of electrophoresis won't be elongated.

Based on the above observations, the inventers discovered that tryptophan, with aromatic structure, is one of the best candidate for the internal standards of CE of thuringiensin among all Amino acids. Pure tryptophan is white crystal and has been characterized as an essential Amino acid with molecule weight 204.22. It's easy to dissolve in water and the solubility is 11.4 g/l at room temperature. It is very stable and won't decompose below 289° C.

The present invention demonstrated the method of quantitative analysis for thuringiensin by capillary electrophoresis (CE), and adding certain concentrations of thuringiensin standards with a fixed amounts of internal standards. The peak area ratio between the testing sample of thuringiensin (the concentration of which is unknown) and the internal standards can be calculated from electropherogram. The linear regression relation can thus be determined. The concentration of thuringiensin in the testing sample can be determined from the peak area ratio and the linear regression formula. Tryptophan is used as the internal standard since it is an aromatic amino acid with the same UV absorption range. It is stable Chemically and easy to procure commercially. It appears earlier than thuringiensin in CE which doesn't affect the electrophoresis time. Tryptophan, some other aromatic amino acids such as tyrosine and phenylalanine are also covered in the present invention because they may have the same function as tryptophan. The concentration of tryptophan, tyrosine and phenylalanine should be between 1 mM and 100 mM. The following application example describes the technical detail.

APPLICATION EXAMPLE

I. Solution Preparation

I-A. Prepare Buffered Solution of MECC (Micellar Electrokinetic Capillary Chromatography)

1. dissolve 1.24 g Boric acid, 3.12 g Dihydrogen Sodium phosphate and 28.84 g SDS (Sodium dodecyl Sulphate ) in 800 ml pure water.
2. Filter the solution with 0.45 $\mu$m membrane filter.
3. Adjust the pH of solution to 9.2 by adding 1N NaOH.
4. Add deionized water till the total volume is 900 ml.
5. Add 10 ml $CH_3CN$ (acetonitrile).
6. Well mix the solution above, filter with 0.45 $\mu$m membrane filter, the final concentration of buffered solution is: 20 mM Dihydrogen Sodium phosphate, 20 mM Boric acid, 100 mM SDS and 10% acetonitrile.

I-B. Preparation of Tryptophan Solution 1. dissolve 100 mg tryptophan in 100 ml deionized water. (the concentration is about 5 mM).
2. filter with 0.45 $\mu$m membrane filter after it completely dissolves.

I-C. Preparation of Thuringiensin Standards

1. Centrifuge (7500 g) the fermentation broth of thuringiensin for 30 min.
2. Filter the upper clear portion of solution with 10,000 MWCO membrane filter and followed by a 1,000 MWCO membrane filter.
3. Add 50% (w/v) activated carbon into the filtered solution.
4. Keep the solution for 10 min without stirring, centrifuge (7500 g) for 30 min.
5. Collect the supernatant and pass it to a preparative HPLC column, and collect the fraction when thuringiensin peak appears.
6. Freeze and dry the fraction fluid.

I-D. Preparation of Mixtures 1. dissolve 50 mg thuringiensin in 1 ml water.
2. Filter the solution with 0.45 $\mu$m membrane filter after it completely dissolves.
3. Dilute the original thuringiensin to one half, repeatedly from 50 mg/ml to 25, 12.5, 6.25 mg/ml.
4. Add equal amount of tryptophan solution into the above 4 different concentrations of thuringiensin solution.

II. Setup of CE

1. Use Beckman p/ACE-2100 capillary.
2. The inner diameter of capillary is 50 $\mu$m, the outer diameter is 365 $\mu$m, the length is 47 cm.
3. The detecting wavelength was set at 254 nm.
4. The voltage is 15 KV.
5. Injection is done by positive pressure for 10 sec.
6. Analyze electropherogram and calculate the peak area by System Gold.

III. Data Processing

1. Deter mine the peak of the purified thuringiensin (made by Pasteur Institute, French and the inventers) from the migration speed of CE.
2. No matter tryptophan is injected into the purified thuringiensin standards alone or mixed with the purified thuringiensin standards together, the migration speed and waveform will not vary.
3. Calculate the peak area ratio between the diluted thuringiensin and tryptophan by computer software.
4. Let the concentration of thuringiensin standards be horizontal coordinate, let the peak area ratio between the thuringiensin standards and tryptophan be vertical coordinate, calculate the regression line and the linear regression formula by EXCEL.

RESULTS

Figure 1:
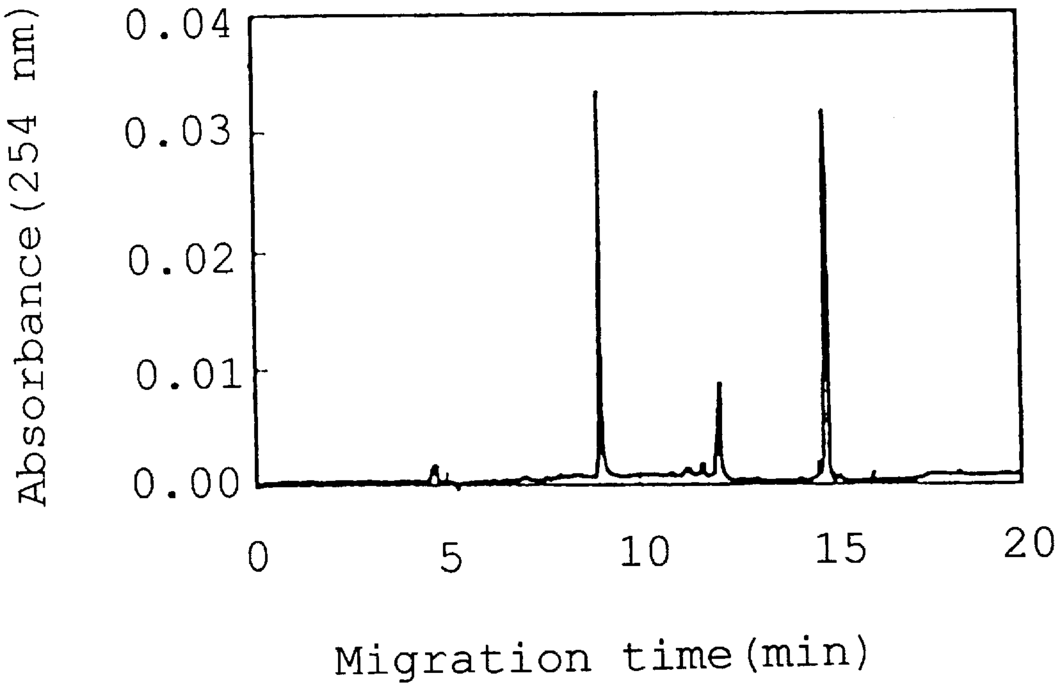
FIG. 1: The electropherograms of 4 different concentrations of thuringiensin secondary standards mixed with the same amount of Tryptophan solution (5 mM), the peak of Tryptophan appeared around 8 min, the peak of thuringiensin appeared around 14 min.
Figure 1:
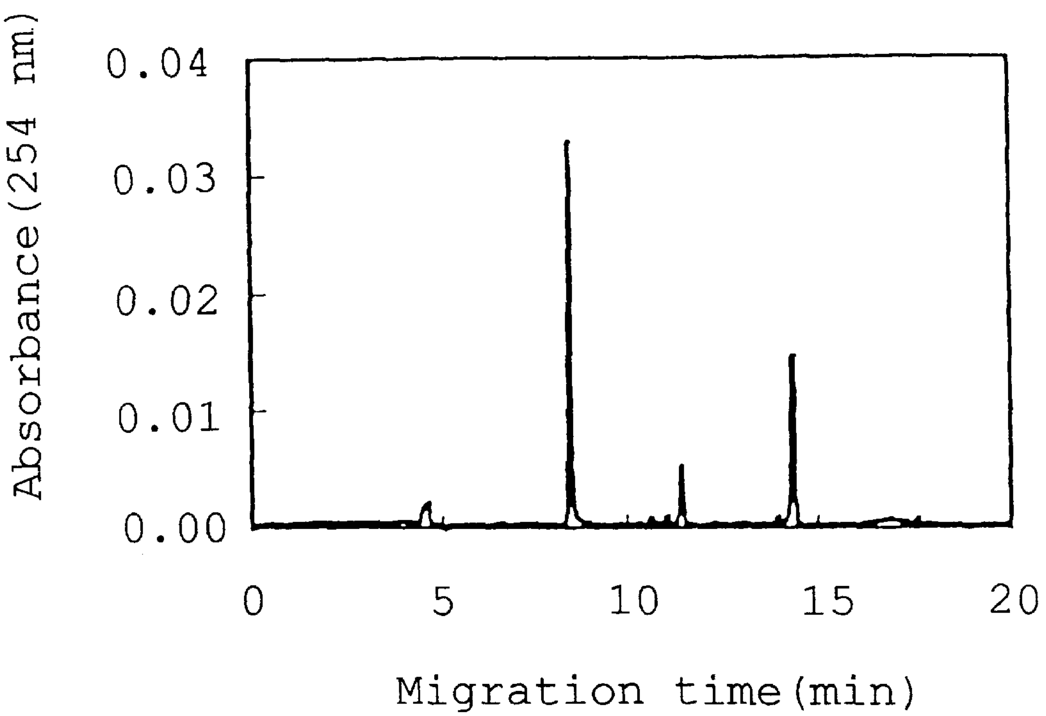
Figure 1:
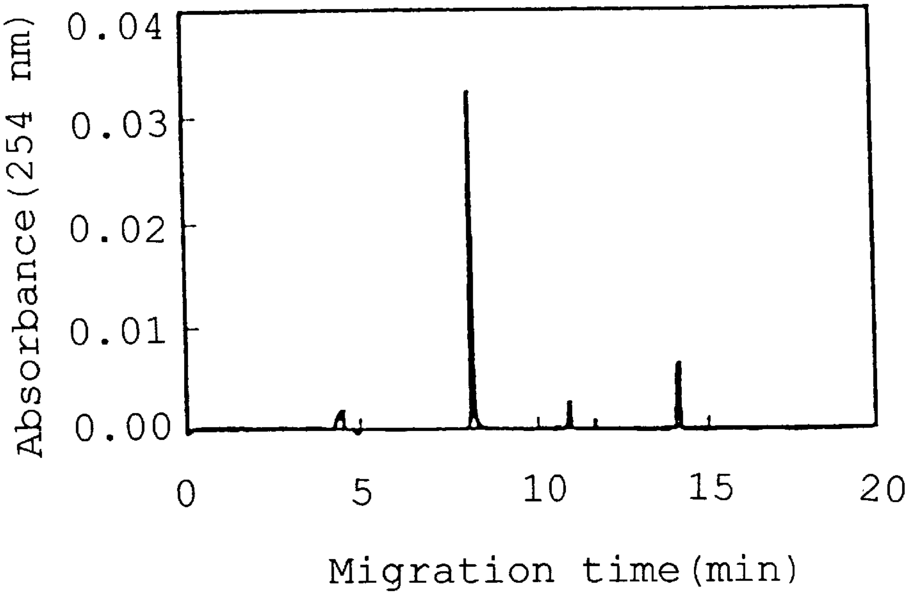
Figure 1:
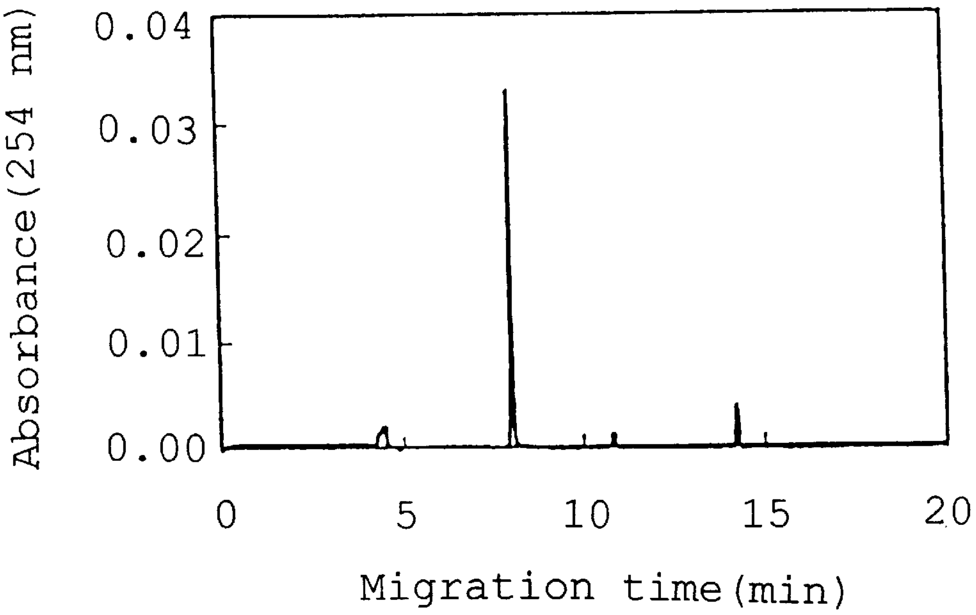

Add equal amount of tryptophan solution (5 mM) into 4 different concentrations of thuringiensin secondary standards (the concentration has been deter mined to be 67 mg/h. w/w). Do CE after the solution is well mixed. The electropherogram is shown in FIG. 1. The peak area of thuringiensin will decrease with the decreasing of its concentration. But the peak area of tryptophan does not vary. Let the peak area ratio between thuringiensin and tryptophan be vertical coordinate, let the concentration of thuringiensin be horizontal coordinate, we can calculate the coefficients of linear regression formula. The result is:

The related coefficient is r=0.9967

The linear regression formula is $$Y=0.0546x-0.026$$

i.e.

$$X=(Y+0.026)/0.0546$$

Y=the peak area ratio between the thuringiensin standards and tryptophan.

The amount of thuringiensin can be calculated from X.

The amount of thuringiensin=X×67/1000.

EXAMPLE 1

Assessment of Thuringiensin in a Semi-purified Thuringiensin Products

Figure 2:
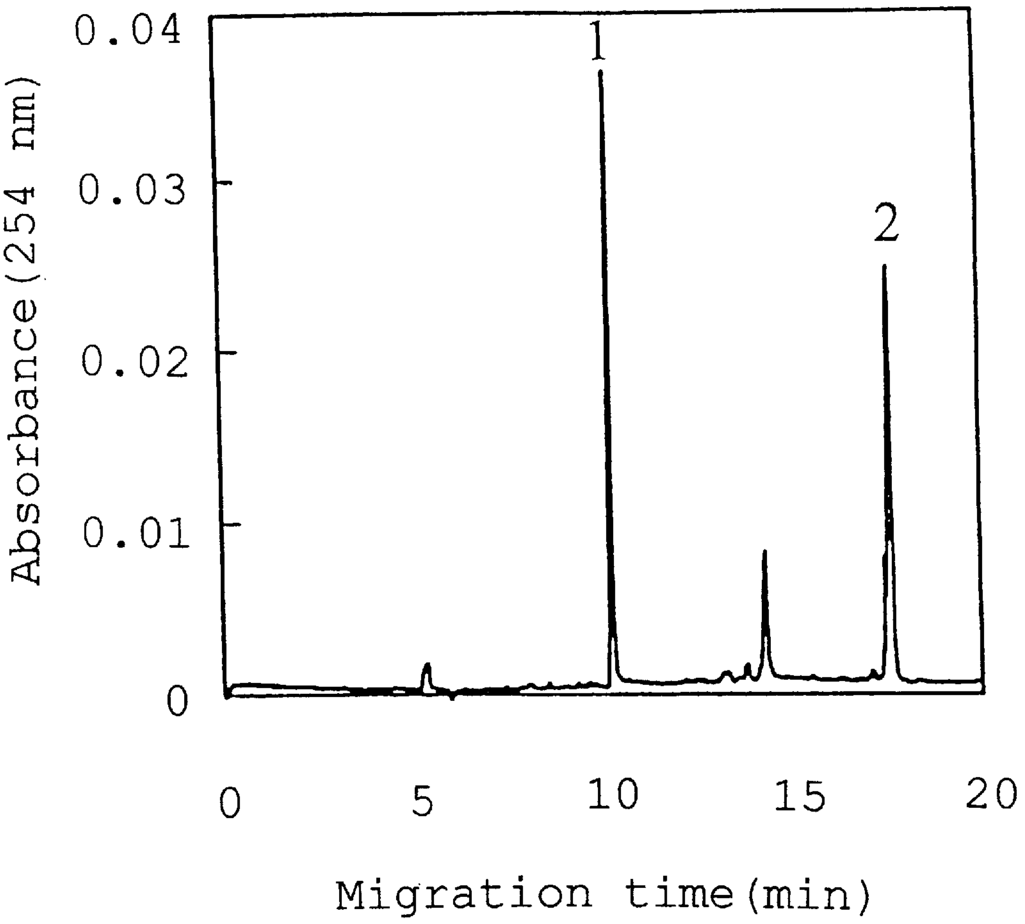
FIG. 2: The electropherograms of semi-purified thuringiensin solutions mixed with the same volume of Tryptophan solution (5 mM).

Dissolve 50 mg semi-purified thuringiensin products in 1 ml buffered Phosphate solution (50 mM, pH 7.0), filter with 0.22 mm membrane filter after dissolving, mix the filtered solution with equal amount of tryptophan (5 mM), then inject the mixture into CE. The electropherogram is shown in FIG. 2. The peak area of thuringiensin as calculated from System Gold software is 3.38867 (arbitrary unit). The peak area of tryptophan is 2.8260, the ratio between them is 1.19758. From the linear regression formula, the relative concentration of thuringiensin can be calculated and equal to 22.41. The actual concentration should be as the following:

$$22.41\times67/1000=1.5015\text{ mg}/25\text{ mg}=60.06\text{ mg/g}.$$

EXAMPLE 2

Assessment of the Concentration of Thuringiensin in a Purified Solution.

Mix 1 ml purified solution with equal amount of tryptophan (5 mM), then subjected for CE injection. The electropherogram is shown in FIG. 3. The peak area is 0.36191 as calculated from software, the peak area is 2.67781, the ratio between them is 0.13515, the relative concentration of thuringiensin is 2.9515 followed the calculation of linear regression formula. Theactual concentration should be as the following:

$$2.9515\times67/1000=0.198\text{ mg}/0.5\text{ mg}=0.396\text{ mg/ml}=396\text{ mg/l}.$$

What is claimed is:

1. A method of quantitative analysis for thuringiensin by capillary electrophoresis, the method comprising:

adding the same concentration of an aromatic amino acid as an internal standard to different concentrations of thuringiensin to create standard samples;

creating an electropherogram for each standard sample;

calculating from the electropherogram for the standard for the standard samples the peak area ratio between the concentration of aromatic amino acid and thuringiensin;

determining the linear regression relation among the peak area ratios; and using the linear regression relation to determine the amount of thuringiensin in a sample.

2. The method of claim 1 in which the aromatic amino acid is selected from the group consisting of tryptophan, tyrosine or phenylalanine.

3. The method of claim 1, wherein the concentration of Amino acid as internal standard is between 1 mM and 100 mM.

* * * * *